United States Patent
Halpaap et al.

(12) 
(10) Patent No.: US 6,720,400 B2
(45) Date of Patent: Apr. 13, 2004

(54) PROCESS FOR THE PREPARATION OF POLYISOCYANATES WITH A BIURET STRUCTURE

(75) Inventors: Reinhard Halpaap, Odenthal (DE); Dieter Mager, Leverkusen (DE); Siegfried Oeckl, Kerpen-Horrem (DE); Harald Mertes, Bridgeville, PA (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/858,057

(22) Filed: May 15, 2001

(65) Prior Publication Data

US 2001/0056169 A1 Dec. 27, 2001

(30) Foreign Application Priority Data

May 22, 2000 (DE) .......................................... 100 25 301

(51) Int. Cl.$^7$ ...................... C08G 18/60; C08G 18/28; C07C 205/00; C07C 229/00; C07C 273/00
(52) U.S. Cl. ........................ 528/48; 528/51; 528/68; 560/169; 560/125; 560/335
(58) Field of Search ................ 560/125, 169, 560/335; 528/51, 45, 48, 68

(56) References Cited

U.S. PATENT DOCUMENTS

| | | | | |
|---|---|---|---|---|
| 3,441,588 A | * | 4/1969 | Wagner et al. | 560/335 |
| 3,903,126 A | * | 9/1975 | Woerner et al. | 560/335 |
| 4,051,165 A | * | 9/1977 | Wagner et al. | 560/335 |
| 4,147,714 A | * | 4/1979 | Hetzel et al. | 560/335 |
| 4,192,936 A | | 3/1980 | Möhring et al. | 528/59 |
| 4,220,749 A | * | 9/1980 | Reichmann et al. | 528/144 |
| 4,340,712 A | * | 7/1982 | Reichmann et al. | 528/45 |
| 4,373,080 A | * | 2/1983 | Reichmann et al. | 528/45 |
| 4,837,359 A | | 6/1989 | Woynar et al. | |
| 5,641,851 A | * | 6/1997 | Wolff et al. | 528/44 |
| 6,066,759 A | | 5/2000 | Heider et al. | |

FOREIGN PATENT DOCUMENTS

DE 196 33 404 2/1998

OTHER PUBLICATIONS

J. Parkt. Chem., 336 (month unavailable) 1994, pp. 185–200, Hans Josef Laas, Reinhard.
Halpaap and Josef Pedain, Zur Synthese aliphatischer Polyisocyanate–Lackpolisocyanate mit Buret–, Isocyanurat– oder Uretdionstruktur.

* cited by examiner

Primary Examiner—Alan L. Rotman
Assistant Examiner—Taylor V Oh
(74) Attorney, Agent, or Firm—Joseph C. Gil; Thomas W. Roy; Gary F. Matz

(57) ABSTRACT

The present invention relates to an improved process for the continuous preparation of polyisocyanates with a biuret structure comprising the steps of continuously reacting excess amounts of organic diisocyanates having exclusively aliphatically and/or cycloaliphatically bound isocyanate groups with organic diamines having exclusively aliphatically and/or cycloaliphatically bound primary amino groups at temperatures above 170° C. and adding acid before or during the reaction.

7 Claims, No Drawings

PROCESS FOR THE PREPARATION OF POLYISOCYANATES WITH A BIURET STRUCTURE

BACKGROUND OF THE INVENTION

The present invention relates to an improved process for the preparation of polyisocyanates with a biuret structure by continuous reaction of excess amounts of organic diisocyanates having exclusively aliphatically and/or cycloaliphatically bound isocyanate groups with organic diamines having exclusively aliphatically and/or cycloaliphatically bound primary amino groups at elevated temperatures in the presence of acids. The polyisocyanates thus prepared are characterised by high stability and good dilutability.

The preparation of aliphatic polyisocyanates with biuret structures has been known since 1958 (DE-A 1 101 394). Possible production processes are described in a review article (Laas et al., J. prakt. Chem. 336, 1994, 185–200) which discusses the advantages and disadvantages of each particular process.

In principle, two processes are distinguished: firstly, the so-called water processes in which the diisocyanates are reacted with water to form ureas and subsequently biurets, and secondly, the so-called diisocyanate/diamine processes in which urea is prepared directly from isocyanate and amine, followed by a biuret reaction. For both processes, as explained in the review article cited above (Laas et al.), numerous variants have been developed and described. In these processes the reaction of hexamethylene diisocyanate (HDI) to HDI biurets is of greatest industrial importance. The biurets are initially in the dissolved form in excess diisocyanate and are separated from excess diisocyanate by distillation and/or extraction and isolated as low-monomer biuret polyisocyanates. Both processes have undergone constant further development and improvement.

Biuret polyisocyanates prepared by water processes are usually characterized by good monomer stability, i.e. stability towards reverse cleavage to free diisocyanates, good dilutability, i.e. stability of dilute solutions towards cloudiness and precipitation under the action of moisture, and outstanding color numbers in view of the relatively mild reaction conditions during preparation. In the biuret formation reactions by the water process, however, by their very principle, a part of the isocyanate groups contained in the reaction mixture is always converted to amino groups by reaction with a biuret forming agent. As the isocyanate groups thus consumed were originally prepared by phosgenation of amino groups, this procedure is less economical. Moreover, the gaseous or liquid by-products such as, carbon dioxide, carbon monoxide, carbonyl sulfide, olefins or nitriles cannot be recycled and have to be disposed of.

Advantages of the refined diisocyanate/diamine processes as described, e.g., in EP-A 277353 (believed to correspond to U.S. Pat. No. 4,837,359) are little or no by-product formation, and no conversion/loss of isocyanate groups to amino groups. A certain disadvantage of biuret polyisocyanates prepared in this way is their slightly reduced monomer stability and reduced dilution stability, with the possibility of slight cloudiness and even precipitates occurring if high dilutions are prepared (<40% solids).

Acid catalysis in biuret polyisocyanate preparation according to the water process catalysis has been known for a relatively long time. More recent research which was published after the publication of Laas et al., J. prakt. Chem. 1994, is described in EP-A 716080 (believed to correspond to U.S. Pat. No. 5,641,851), WO 97/03044 (believed to correspond to U.S. Pat. No. 6,066,759) and DE-A 19633404. EP-A 716080 discloses that the addition of OH acid compounds such as, e.g., dialkyl phosphates, suppresses the formation of insoluble urea during the biuret forming reaction of aliphatic diisocyanates with water. DE-A 19633404, teaches that the diisocyanates are reacted in special mixing components with a high shear action. The document also mentions acid (dialkyl phosphate)-catalyzed reactions in those examples where water or tert.-butanol, optionally in mixture with diamine, are used as reactants. Examples of this application (Ex. 1, Table 1 and Ex. 2, Table 2) with HDI and HDA were carried out without acid catalysis using the special mixing components.

An object of the present invention is to continuously prepare polyisocyanates with a biuret structure with improved properties while retaining the simple (economically most advantageous) diisocyanate/diamine process. An additional object of the invention is, in particular, to prepare biuret polyisocyanates with improved monomer stability and optimum dilutability in organic solvents by such a continuous process without the occurrence of cloudiness or precipitation. Moreover, polyisocyanates with a biuret structure prepared according to the invention should exhibit little sensitivity to moisture and should have low color numbers. It should be possible to dispense with the need to use special mixing apparatus to produce high shear forces.

Surprisingly, as has now been found, it is possible to prepare, in a continuous process, high-quality polyisocyanates with a biuret structure based on organic diisocyanates having exclusively aliphatically and/or cycloaliphatically bound isocyanate groups and organic diamines having exclusively aliphatically and/or cycloaliphatically bound primary amino groups with improved properties and without the use of special mixing apparatus if the starting materials are caused to react with one another at temperatures above 170° C. with the addition of acids.

This finding is extremely surprising since the use of OH acids in diisocyanate/diamine direct processes led one to assume that, prior to biuret formation proper, the OH acid is neutralized by the amine used and thus becomes ineffective. Moreover, it was to be assumed that the OH acid is attacked by the isocyanate and withdrawn at least partially from the reaction by conversion to the anhydride. In the above-mentioned water processes, this process of becoming ineffective is not a problem because the acid can be re-formed repeatedly by the addition of water. Consequently, it was utterly unexpected that the addition of acids in the simple (economically attractive) diisocyanate/diamine process would bring a series of important advantages:

the monomer stability of the biuret polyisocyanates produced can be markedly improved;
the sensitivity of the biuret polyisocyanates produced towards damp solvents can be decidedly reduced;
the required reaction temperature of the reaction of diisocyanate with diamine can be reduced without prolonging the reaction time and without the intermediate occurrence of cloudiness (polyureas), which results in a considerable energy saving.

SUMMARY OF THE INVENTION

The invention relates to a process for the continuous preparation of polyisocyanates with a biuret structure by continuously reacting excess amounts of organic diisocyanates having exclusively aliphatically and/or cycloaliphatically bound isocyanate groups with organic diamines having exclusively aliphatically and/or cycloaliphatically bound primary amino groups at temperatures above 170° C. and adding acid during the reaction.

DETAILED DESCRIPTION OF THE INVENTION

The starting materials for the process according to the invention are organic diisocyanates having exclusively aliphatically and/or cycloaliphatically bound isocyanate groups and a molecular weight below 300. Examples of such diisocyanates include 1,4-diisocyanatobutane, 1,6-diisocyanatohexane (hexamethylene diisocyanate, HDI), 1,6-diisocyanato-2,2,4-trimethylhexane and/or 1,6-diisocyanato-2,4,4-trimethylhexane, 1,4-and/or 1,5-diisocyanatohexane, 2,6-diisocyanatohexanoic acid ethyl ester, 1,12-diisocyanatododecane, 1,4-diisocyanatocyclohexane, 2,4- and/or 2,6-diisocyanato-1-methylcyclohexane, 1-isocyanato-3,3,5-trimethyl-5-isocyanatomethylcyclohexane (isophorone diisocyanate, IPDI), 1,3- and/or 1,4-bis-(isocyanatomethyl)cyclohexane, 4,4'-diisocyanatodicyclohexylmethane or 6-isocyanatohexanoic acid-2-isocyanatoethyl ester. Any mixtures of such diisocyanates may also be used. 1,6-diisocyanatohexane is preferred.

Further starting materials for the process according to the invention are organic diamines having exclusively aliphatically and/or cycloaliphatically bound primary amino groups. They preferably have a molecular weight below 300. Examples include 1,2-diaminoethane, 1,2-diaminopropane, 1,3-diaminopropane, 1,4-diaminobutane, 1,6-diaminohexane, 1,6-diamino-2,2,4-trimethylhexane and/or 1,6-diamino-2,4,4-trimethylhexane, 1,4- and/or 1,5-diaminohexane, 2,4- and/or 2,6-diamino-1-methylcyclohexane, 1-amino-3,3,5-trimethyl-5-aminomethylcyclohexane, 1,3- and/or 1,4-bis(aminomethyl)cyclohexane or 4,4'-diaminodicyclohexylmethane. Any mixtures of such diamines may also be used. 1,6-diaminohexane is preferred.

In the process according to the invention the above-mentioned starting diisocyanates and diamines are reacted in equivalent ratios of isocyanate groups to amino groups of at least 4:1, preferably from 4:1 to 25:1 and more preferably from 7:1 to 20:1, wherein the primary amino groups are treated in the calculation as monofunctional groups.

Catalysts used according to the process of the invention include any acids, preferably protonic acids with a pKa value of <10. Preferred acid catalysts include phosphoric acid or phosphates such as methyl phosphate, ethyl phosphate, n-butyl phosphate, n-hexyl phosphate, 2-ethylhexyl phosphate, isooctyl phosphate, n-dodecyl phosphate, dimethyl phosphate, diethyl phosphate, di-n-propyl phosphate, di-n-butyl phosphate, di-n-amyl phosphate, diisoamyl phosphate, di-n-decyl phosphate, diphenyl phosphate or dibenzyl phosphate; sulfonic acids such as methanesulfonic acid, ethanesulfonic acid, propanesulfonic acid, 2 and 4-toluenesulfonic acid or naphthalene-1-sulfonic acid; or mono- and dicarboxylic acids such as formic acid, acetic acid, propionic acid, butyric acid, pivalic acid, stearic acid, cyclohexane carboxylic acid, oxalic acid, malonic acid, succinic acid, adipic acid, benzoic acid or phthalic acid. Dialkyl phosphates of the above-mentioned kind are more preferred. A preferred dialkyl phosphate is di-n-butyl phosphate.

These acids may be used in amounts from 0.01 wt. % to 1.0 wt. %, preferably from 0.02 wt. % to 0.5 wt. % and more preferably from 0.05 wt. % to 0.5 wt. %, based on the total amount of starting diisocyanates used. The acids may be added in dissolved form in a suitable solvent. The acids are added preferably in bulk.

The process according to the invention is carried out preferably in the absence of solvents. The use of suitable solvents which are inert under the reaction conditions is possible. Examples of suitable solvents include hexane, ethyl acetate, butyl acetate, 1-methoxypropyl-2-acetate, propylene glycol diacetate, 2-butanone, 4-methyl-2-pentanone, cyclohexanone, toluene, xylene, relatively highly substituted aromatics (for example, Solvent naphtha, Solvesso, Isopar, Nappar (Deutsche EXXON CHEMICAL GmbH, Cologne) and Shellsol (Deutsche Shell Chemie GmbH, Eschborn)); or trialkyl phosphates such as trimethyl phosphate, and any mixtures of such solvents.

The starting materials are reacted immediately after they have been mixed, at a temperature above 170° C., preferably above 200° C., particularly from 230° C. to 320° C. These high reaction temperatures at the beginning of the reaction may be reached by pre-heating the diisocyanate to temperatures above 160° C., preferably above 220° C. If a large diisocyanate excess is used, it is often unnecessary to pre-heat the diamines, but these are generally also pre-heated to about 50° C. to 200° C. As a rule it may be assumed that the reaction mixture, even in the absence of any heating of the mixing vessel, will heat up immediately after its preparation by mixing the starting materials because of the strong heat effect of the spontaneously occurring reaction, namely to a temperature which is about 20° C. to 70° C. above the temperature that can be expected due to heating the starting materials, without incorporating the heat effect. The heating temperature of the starting materials required to ensure the high temperatures that are important for the invention may be estimated in a good approximation from the specific heat of the starting materials (about 0.5 kcal/kg K) and the reaction enthalpy of the reaction (about 35 kcal/mole) and may also be determined, if necessary, by a preliminary test.

The heating of the diisocyanates required in any case must be brought about within the shortest possible time, preferably within a period of less than 30 seconds, on account of the known heat sensitivity of these compounds. This is achieved by using appropriate heat exchange units known from the prior art. The heat exchangers may be arranged, e.g. as tubes, tube bundles or plate heat exchangers. They may be operated with a liquid heating medium, with pressurized steam or with direct electric heating. Heat exchangers which allow the heating process of the starting diisocyanates to take place within a period of less than 3 seconds are preferred.

The continuous streams of reactants can be combined in a mixing chamber after the preliminary heating described. There are no particular requirements for a special efficiency of the mixing chamber, such as intensive mixing of the components any static or dynamic equipment known from the prior art may be used. Even a simple reaction tube without any built-in components, at one end of which the reaction components are introduced co-currently, is sufficient and used preferably as a mixing chamber.

The entry points of the components and exit points of the reaction mixture are preferably in the form of apertured plates or nozzles so that the feed may be carried out at a pressure above atmospheric. As a result, it is possible to ensure that the reaction mixture does not enter the diisocyanate and diamine feed lines. To this end, the cross-sections are selected in such a way that a pressure from 1.5 bar to 100 bar, preferably from 1.5 bar to 40 bar builds up in each case on the feed lines. The form and arrangement of the nozzles and/or apertured plates and high pressure are not important for the process according to the invention because the requirements in respect of the mixing efficiency are not stringent.

The acid feed takes place preferably in the region of the mixing chamber, preferably into the isocyanate components immediately prior to the amine feed. Conventional pumps known from the prior art, such as reciprocating or reciprocating diaphragm pumps may be used for feeding the acids. It is merely necessary that the feed pressure is higher than the mixing chamber pressure.

After passing through the mixing chamber and the residence time zone optionally arranged downstream of the mixing chamber, the reaction mixture is cooled continuously by suitable heat exchangers within not more than 10 minutes, preferably not more than 5 minutes. The cooling can be done steadily or in stages to a temperature within the temperature range from 80° C. to 220° C., preferably 120° C. to 200° C. Within these temperature ranges, the reaction mixture can be subjected to a thermal after-treatment by means of a suitable post-reactor, preferably for a period of not more than 5 hours, more preferably not more than 2 hours, particularly up to 30 minutes. Above all, it is important that the reaction mixture is exposed to the maximum temperatures of over 170° C., preferably over 200° C., more preferably over 230° C., for only a short time. The residence times in this maximum temperature range should be in the region of minutes to seconds, preferably below 60 seconds. The duration of the thermal after-treatment may vary widely. A comparatively long thermal after-treatment is required at low temperatures, and a comparatively short thermal after-treatment is required at high temperatures.

The thermal after-treatment may be carried out, for example, in reactors arranged in the form of a cascade, or in continuous-flow agitated boilers.

After the thermal after-treatment, the reaction product is in the form of a solution of biuret group-containing polyisocyanates in excess starting diisocyanate and optionally used solvents, unless these have already been distilled off during the reaction. Volatile constituents (excess diisocyanate monomer and optionally used solvents) are then generally removed from the mixture by distillation under high vacuum, preferably in a thin film evaporator, for example, at a temperature from 100° C. to 200° C., preferably from 120° C. to 180° C.

In another embodiment of the process according to the invention, the volatile constituents are separated from the reaction product by extraction with suitable solvents which are inert towards isocyanate groups, for example, aliphatic or cycloaliphatic hydrocarbons such as pentane, hexane, heptane, cyclopentane or cyclohexane.

High-quality polyisocyanates with a biuret structure with a diisocyanate content of at most 0.5 wt. %, preferably at most 0.3 wt. %, are obtained in this way.

The biuret group-containing polyisocyanates prepared according to the process of the invention, particularly those which were prepared with the exclusive use of 1,6-diisocyanatohexane and 1,6-diaminohexane as starting materials, are valuable starting materials for the preparation of two-component polyurethane coating compositions. The products prepared according to the invention have good color numbers and comparatively low viscosities. In contrast to the biuret polyisocyanates of the prior art, they are also characterized by considerably improved monomer stability, lower sensitivity to moisture and a markedly improved dilutability with organic solvents.

EXAMPLES

In the Examples below, all the percentage details refer to percentages by weight.

Example 1

(Comparison according to EP-A 277 353, believed to correspond to U.S. Pat. No. 4,837,359)

In a test apparatus for the continuous preparation of biuret polyisocyanates, 667 parts per hour of hexamethylene diisocyanate (HDI) were fed continuously through a reaction mixing chamber at 250° C. 27 parts per hour of hexamethylene diamine (HDA) were then also fed continuously into this mixing chamber, the temperature in the mixing chamber rising to 275° C. due to the heat of reaction. After leaving the mixing chamber, the product was cooled to 180° C. within a few seconds and after-treated for a few minutes at 180° C.–140° C. Excess HDI was then separated from the crude product thus obtained by conventional thin film distillation technology. A biuret polyisocyanate suitable as a lacquer hardener and having the following characteristic data was obtained:

NCO: 22.0%
Viscosity: 10,000 mPas (23° C.)

Example 2

(according to the invention)

Operations were carried out initially with the same amounts as those described in Example 1 except that a continuous stream of 1 part per hour of di-n-butyl phosphate (DBP) was injected additionally into the HDI feed shortly before the mixing chamber. The mixing chamber temperature rose as a result by 5° C. to 280° C. Excess HDI was removed from the crude product thus obtained by conventional thin film distillation technology, as described in Example 1, and a biuret polyisocyanate 2a with the following characteristic data was obtained:

NCO: 21.8%
Viscosity: 11,100 mPas (23° C.)

The less favorable higher viscosity of the product prepared according to the invention compared with the polyisocyanate from Example 1 could be adjusted very easily to the viscosity data of the biuret polyisocyanate prepared without the use of a catalyst by reducing the HDI inflow temperature from 250° C. to 230° C. As a result of this measure, a product 2b with the following characteristic data was obtained:

NCO: 22.1%
Viscosity: 9,520 (23° C.)

The process according to the invention thus made it possible to reduce the reaction temperature, compared with the uncatalyzed production process, resulting in a considerable energy saving for heating HDI.

Example 3

(comparison according to EP-A 277 353)

Immediately after the preparation of biuret polyisocyanates 2a and 2b according to the invention and while maintaining the continuous mode of operation with constant mass flows of HDI and HDA, the DBP feed was ended and the HDI inflow temperature was raised again to 250° C. After the crude product had been worked up by thin film distillation, a product with the following characteristic data was obtained:

NCO: 22.1%
Viscosity: 10,200 mPas (23° C.)

Example 4

(testing the storage stability)

In order to examine the storage stability, samples of the biuret polyisocyanates from Example 1 to 3 were stored for 4 weeks at 35° C. The Table below shows the monomeric HDI contents which were measured in each case before hot storage and after 2 and 4 weeks. The comparison showed that the samples prepared according to the invention with the addition of DBP had a markedly lower tendency to reverse cleavage.

|  | HDI [%] | | |
| --- | --- | --- | --- |
| Sample | Initial value | After 2 weeks 35° C. | After 4 weeks 35° C. |
| Example 1 | 0.31 | 0.43 | 0.50 |
| Example 2b/sample 1 | 0.21 | 0.26 | 0.24 |
| Example 2b/sample 2 | 0.23 | 0.33 | 0.34 |
| Example 2b/sample 3 | 0.21 | 0.32 | 0.29 |
| Example 3 | 0.20 | 0.39 | 0.44 |

Example 5

(testing the dilutability)

The biuret polyisocyanates from Example 1 (comparison) and Example 2b (according to the invention) were diluted in each case with butyl acetate to form polyisocyanate solutions having a 75% solids content. The butyl acetate, like all the solvents used hereinafter, was dehydrated beforehand with molecular sieve (type: Baylith® SV 133; Bayer A G, Leverkusen).

The biuret solutions were adjusted by dilution in each case to solids contents of 35%, 30%, 25% and 20% with the solvents or solvent mixtures listed below. The solutions were stored in sealed bottles for 28 days at 50° C. or for 4 months at room temperature (RT) and the dilution stability was then assessed visually. In the assessment, a distinction was made between 0 for unchanged, 1 for slight cloudiness or sediment, and 2 for substantial cloudiness or sediment.

The Table below shows the results of storage at 50° C. (28 days).

| Polyisocyanate from | Example 1 (comparison) | | | | Example 2b (acc. to the invention) | | | |
| --- | --- | --- | --- | --- | --- | --- | --- | --- |
| Solids content | 35% | 30% | 25% | 20% | 35% | 30% | 25% | 20% |
| MPA | 1 | 2 | 2 | 2 | 0 | 0 | 0 | 0 |
| BA/SN (1:2) | 0 | 2 | 2 | 2 | 0 | 0 | 0 | 1 |
| X | 0 | 2 | 2 | 2 | 0 | 0 | 0 | 1 |
| BA | 0 | 0 | 1 | 2 | 0 | 0 | 0 | 1 |
| MPA/X (1:1) | 0 | 0 | 0 | 1 | 0 | 0 | 0 | 0 |
| EA | n.d. | 1 | n.d. | 2 | n.d. | 0 | n.d. | 1 |

Abbreviations:
MPA = 1-methoxypropyl-2-acetate
BA = butyl acetate
SN = Solvent naphtha ® 100
X = xylene
EA = ethyl acetate
n.d. = not determined.

The Table below shows the results of storage at room temperature (4 months).

| Polyisocyanate from | Example 1 (comparison) | | | | Example 2b (acc. to the invention) | | | |
| --- | --- | --- | --- | --- | --- | --- | --- | --- |
| Solids content | 35% | 30% | 25% | 20% | 35% | 30% | 25% | 20% |
| MPA | 2 | 2 | 2 | 2 | 1 | 0 | 0 | 0 |
| BA/SN (1:2) | 0 | 2 | 2 | 2 | 0 | 0 | 0 | 0 |
| X | 0 | 2 | 2 | 2 | 0 | 0 | 0 | 2 |
| BA | 1 | 2 | 2 | 2 | 1 | 1 | 1 | 1 |
| MPA/X (1:1) | 0 | 0 | 2 | 2 | 0 | 0 | 0 | 0 |
| EA | n.d. | 2 | n.d. | 2 | n.d. | 1 | n.d. | 1 |

Example 6

(according to the invention 6a and comparison 6b)

A mixture of 302.4 g of HDI, 157 g of cyclohexane and 0.45 g of DBP was charged to a 1 liter four-necked flask with a Taler stirrer, thermometer and distillation column at room temperature under a gentle stream of nitrogen. A solution of 11.6 g of HDA and 157 g of cyclohexane at a maximum temperature of 30° C. was then added within a few seconds with thorough stirring. The temperature rose only a little and the resulting urea emulsion remained readily stirrable. The mixture was then heated to 180° C. and the cyclohexane was distilled. After about 1.5 to 2 hours, the urea had dissolved. Stirring was continued for another 4 hours at 180° C. Isocyanate monomer was then removed from the crude solution in a commercial short way thin film evaporator at a temperature of 130° C. and a pressure of 0.1 mbar. A clear, practically colorless biuret polyisocyanate 6a with the following characteristic data was obtained:
NCO: 21.6%
Viscosity: 9,700 mPas (23° C.)

For comparison, a biuret polyisocyanate was prepared according to the same process but without the addition of DBP. The clear, practically colorless product 6b had the following characteristic data:
NCO: 21.7%
Viscosity: 9,500 mPas (23° C.)

In order to examine the storage stability, both biuret polyisocyanates were stored at various temperatures for up to 12 weeks. The Table below shows the starting HDI monomer contents, and the values which were determined after storage at high temperature and at room temperature.

|  | HDI [%] | | | |
| --- | --- | --- | --- | --- |
| Biuret polyisocyanate | Start | 1 week 80° C. | 6 weeks 50° C. | 12 weeks RT |
| Acc. to invention 6a | 0.18 | 0.58 | 0.48 | 0.48 |
| Comparison 6b | 0.21 | 0.88 | 0.84 | 0.85 |

Example 7

(according to the invention 7a and comparison 7b)

134.4 g of HDI were charged to a 250 ml four-necked flask with a Taler stirrer, thermometer and condenser at 240° C. under a gentle stream of nitrogen. 0.34 g of DBP and immediately afterwards 4.6 g of HDA at a temperature of about 80° C. were added within a few seconds, with thorough stirring. The temperature of the mixture rose rapidly to about 255° C. The urea dissolved immediately. The mixture was allowed to cool to 170° C. and was then stirred for another 30 minutes. HDI monomer was then removed from the crude solution, which had an NCO content of 41.0%, by thin film distillation at 130° C. under a high vacuum. A clear, practically colorless biuret polyisocyanate 7a with the following characteristic data was obtained:

NCO: 21.6%
Viscosity: 13,200 mPas (23° C.)

For comparison, a biuret polyisocyanate was prepared according to the same process but without the addition of DBP. After thin film distillation of the crude solution (NCO content 42.0%), a clear, practically colorless product 7b with the following characteristic data was obtained:

NCO: 21.7%
Viscosity: 12,500 mPas (23° C.)

In order to examine the storage stability, both biuret polyisocyanates were stored for 1 week at 80° C. The Table below shows the starting HDI monomer contents and the values which were determined after storage at high temperature and at room temperature.

| Biuret polyisocyanate | HDI [%] | |
|---|---|---|
| | Start | 1 week, 80° C. |
| According to invention 7a | 0.15 | 0.45 |
| Comparison 7b | 0.78 | 1.90 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the continuous preparation of polyisocyanates with a biuret structure comprising the steps of continuously reacting excess amounts of organic diisocyanates having exclusively aliphatically and/or cycloaliphatically bound isocyanate groups with organic diamines having exclusively aliphatically and/or cycloaliphatically bound primary amino groups at temperatures above 170° C. and adding acid to the diisocyanate before the diamine feed;

wherein the organic diisocyanates are selected from the group consisting of 1,4-diisocyanatobutane, hexamethylene diisocyanate, 1,6-diisocyanato-2,2,4-trimethylhexane, 1,4-diisocyanatohexane, 1,5-diisocyanatohexane, 2,6-diisocyanatohexanoic acid ethyl ester, 1,12-diisocyanatododecane, 1,4-diisocyanatocyclohexane, 2,4- and/or 2,6-diisocyanato-1-methylcyclohexane, 1-isocyanato-3,3,5-trimethyl-5-isocyanatomethylcyclohexane, 1,3-bis-(isocyanatomethyl)cyclohexane, 1,4-bis-(isocyanatomethyl)cyclohexane, 4,4'-diisocyanatodicyclo-hexylmethane, 6-isocyanatohexanoic acid-2-isocyanatoethyl ester, and mixtures thereof; and wherein the organic diamines are selected from the group consisting of 1,2-diaminoethane, 1,2-diaminopropane, 1,3-diaminopropane, 1,4-diaminobutane, 1,6-diaminohexane, 1,6-diamino-2,2,4-trimethylhexane, 1,6-diamino-2,4,4-trimethylhexane, 1,4-diaminohexane, 1,5-diaminohexane, 2,4-diamino-1-methylcyclohexane, 2,6-diamino-1-methylcyclohexane, 1-amino-3,3,5-trimethyl-5-aminomethylcyclohexane, 1,3-bis(aminomethyl)cyclohexane, 1,4-bis(aminomethyl)cyclohexane, 4,4'-diaminodicyclohexylmethane and mixtures thereof.

2. The process of claim 1 wherein the acid comprises a member selected from the group consisting of phosphoric acids, sulfonic acids and carboxylic acids.

3. The process of claim 1 wherein the acid comprises phosphoric acid dialkyl ester.

4. The process of claim 1 wherein the acid is added in amounts from 0.01 wt. % to 1.0 wt. %, based on diisocyanate used.

5. The process of claim 1 wherein the organic diisocyanate is hexamethylene diisocyanate (HDI) and the organic diamine is hexamethylene diamine (HDA).

6. The process of claim 1 wherein said temperature is above 200° C.

7. The process of claim 1 further comprising removing excess diisocyanate from the polyisocyanate solution by extraction or thin film distillation until a diisocyanate monomer contents of <0.5 wt. % is obtained.

* * * * *